(12) United States Patent
Danhof

(10) Patent No.: US 8,604,187 B2
(45) Date of Patent: Dec. 10, 2013

(54) COMPOSITIONS AND METHODS OF ALOE POLYSACCHARIDES

(75) Inventor: Ivan E. Danhof, Grand Prairie, TX (US)

(73) Assignee: North Texas Medical Associates, Grand Prairie, TX (US)

(*) Notice: Subject to any disclaimer, the term of this patent is extended or adjusted under 35 U.S.C. 154(b) by 278 days.

(21) Appl. No.: 12/985,943

(22) Filed: Jan. 6, 2011

(65) Prior Publication Data

US 2011/0172181 A1 Jul. 14, 2011

Related U.S. Application Data

(60) Provisional application No. 61/294,970, filed on Jan. 14, 2010.

(51) Int. Cl.
*C08B 37/00* (2006.01)

(52) U.S. Cl.
CPC ......... *C08B 37/0003* (2013.01); *C08B 37/0006* (2013.01)
USPC ........................................ 536/128

(58) Field of Classification Search
None
See application file for complete search history.

(56) References Cited

U.S. PATENT DOCUMENTS

| | | | | |
|---|---|---|---|---|
| 4,735,935 | A * | 4/1988 | McAnalley | 514/53 |
| 5,106,616 | A | 4/1992 | McAnalley et al. | |
| 5,118,673 | A | 6/1992 | Carpenter et al. | |
| 5,703,060 | A | 12/1997 | McAnalley et al. | |
| 5,902,796 | A * | 5/1999 | Shand et al. | 514/54 |
| 6,083,508 | A | 7/2000 | Avalos et al. | |
| 7,196,072 | B2 | 3/2007 | Pasco et al. | |
| 2003/0096378 | A1 | 5/2003 | Qiu et al. | |
| 2006/0084629 | A1 | 4/2006 | Needleman et al. | |

FOREIGN PATENT DOCUMENTS

| WO | 9001253 A1 | 2/1990 |
|---|---|---|
| WO | 2012094010 A1 | 7/2012 |

OTHER PUBLICATIONS

Acemannan Immunostimulant, "Acemannan Immunostimulant Veterinary Information from Drugs.com," http://www.drugs.com/vet/acemannan-immunostimulant.html, May 24, 2011, 3 pages.
Egger, Stefan F., "Hematopoietic Augmentation by a B-(1,4)-Linked Mannan," Cancer Immunol. Immunother, (1996), 43:195-205.
International Search Report and Written Opinion for PCT/US2011/020402, Dated Mar. 31, 2011, 12 pages.
Peng, S.Y., et al., "Decreased Mortality of Norman Murine Sarcoma in Mice Treated with the Immunomodulator, Acemannan," Molecular Biotherapy, (1991), vol. 3, pp. 79-87.
Pugh, Nirmal, et al., "Characterization of Aloeride, a New High-Molecular-Weight Polysaccharide from Aloe Vera with Potent Immunostimulatory Activity," (2001), J. Agric. Food Chem., vol. 49, pp. 1030-1034.
Wang, Shu-hua, "Isolation, Purification and Analysis of Polysaccaride from Aloe," Jiangsu Chemical Industry, Oct. 2007, vol. 35, No. 5, pp. 15-18.
Xia, Pi, W., et al., "Purification Process of Aloe Polysaccharide and its Anti-tumor Activity in vitro," Chin. J. Nat. Med., Nov. 2007, vol. 5, No. 6, pp. 425-427.
Xiaolan, Fu, et al., "The Study Situation on Chemical Composition of Aloe," www.gdchem.com, Oct. 2008, 35:186, pp. 99-102.
Zhang, Su-Ian, "Research Progress on the Immunoregulation Activity of Aloe Polysaccharide," Journal of Anhui. Agri. Sci., 2009, 37(32):15837-15838.
Search Report, Taiwan Patent Application No. 100101562 dated Nov. 26, 2012.
Sun-A Im, et al., "Identification of optimal molecular size of modified Aloe polysaccharides with maximum immunomodulatory activity," International Immunopharmacology, 2005, vol. 5:2, pp. 271-279.

* cited by examiner

*Primary Examiner* — Eric S Olson
(74) *Attorney, Agent, or Firm* — Edwin S. Flores; Chainey P. Singleton; Chalker Flores, LLP

(57) ABSTRACT

The present invention describes a method for preparing a polymannan extract from freeze-dried *aloe* powder. The polymannan extract of the present invention is further used to formulate a sterile injectable formulation for the treatment of one or more cancers, leukemias and lymphomas, prostate cancer, breast cancer, and colon cancer, immune diseases, particularly immune related neoplasms, acquired immune deficiency syndrome, and hepatitis C.

18 Claims, 10 Drawing Sheets

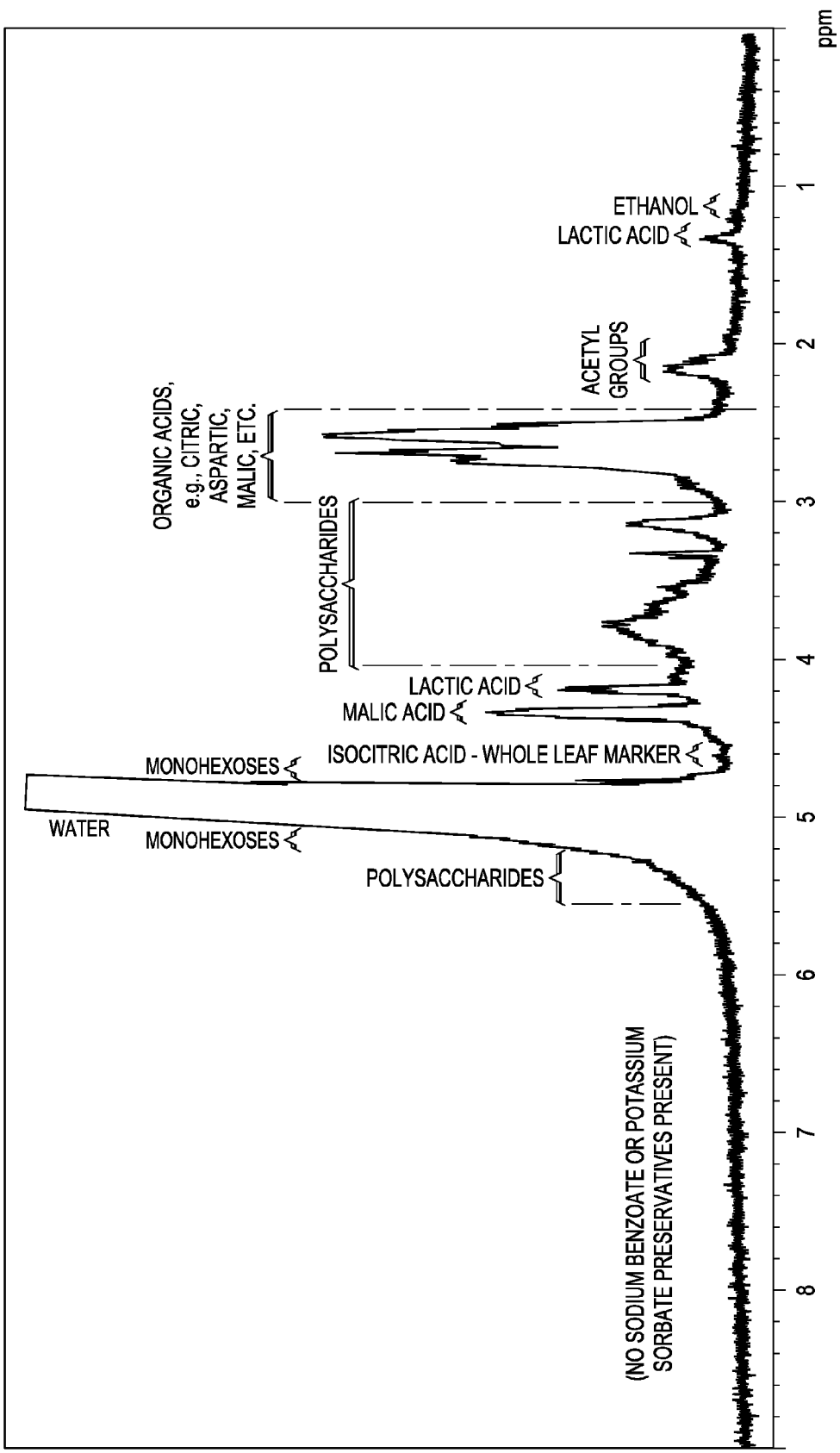

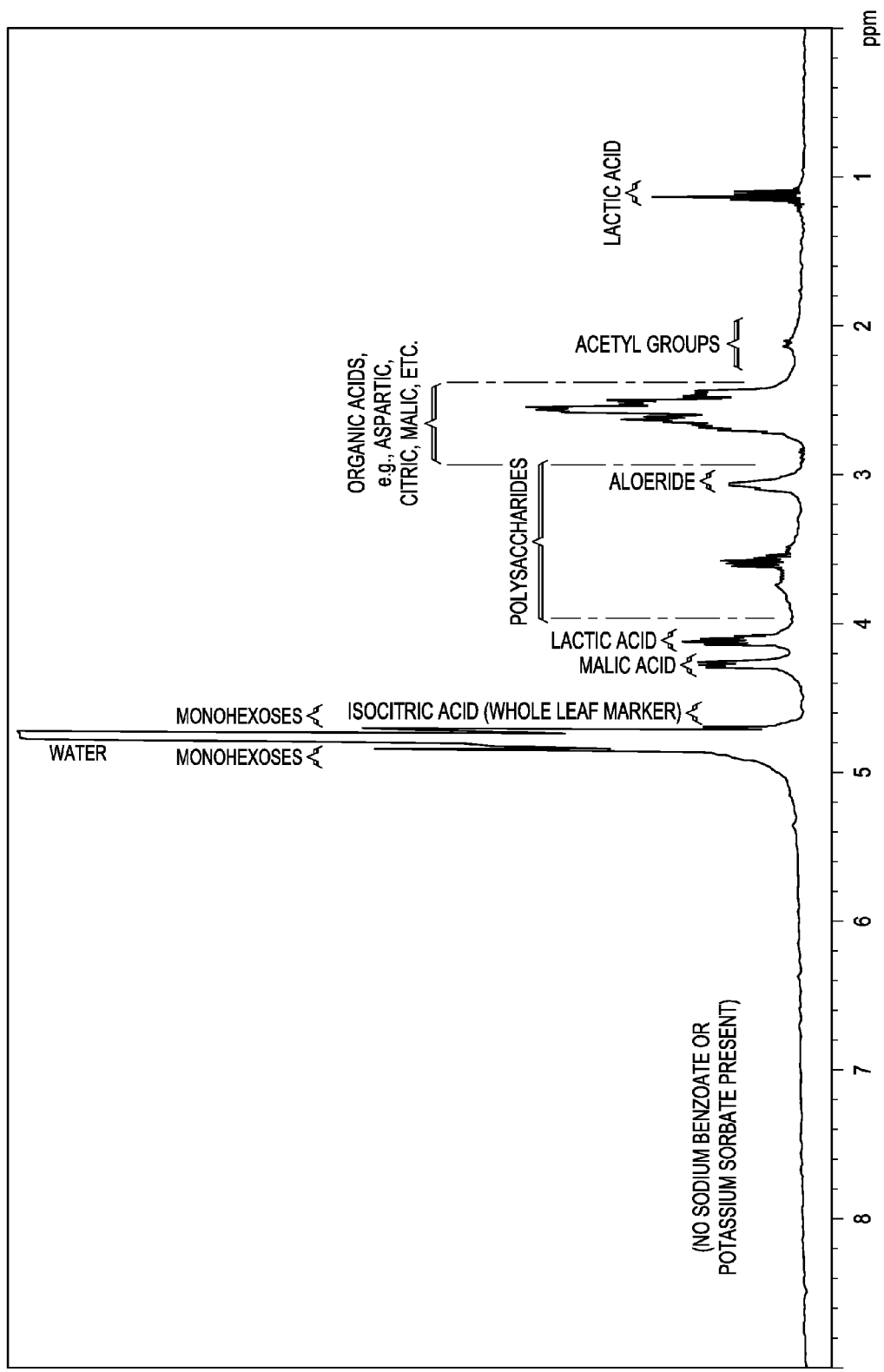

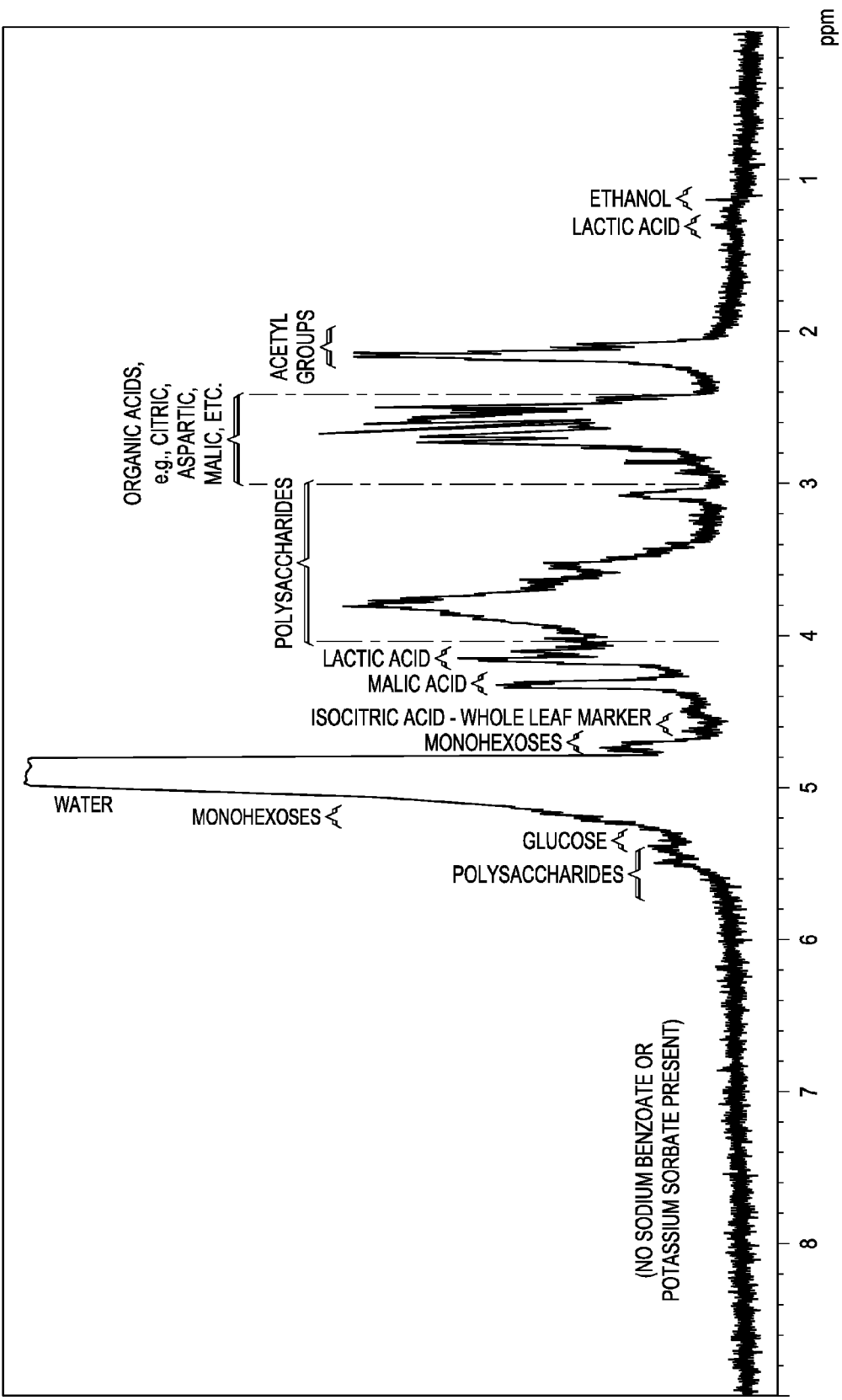

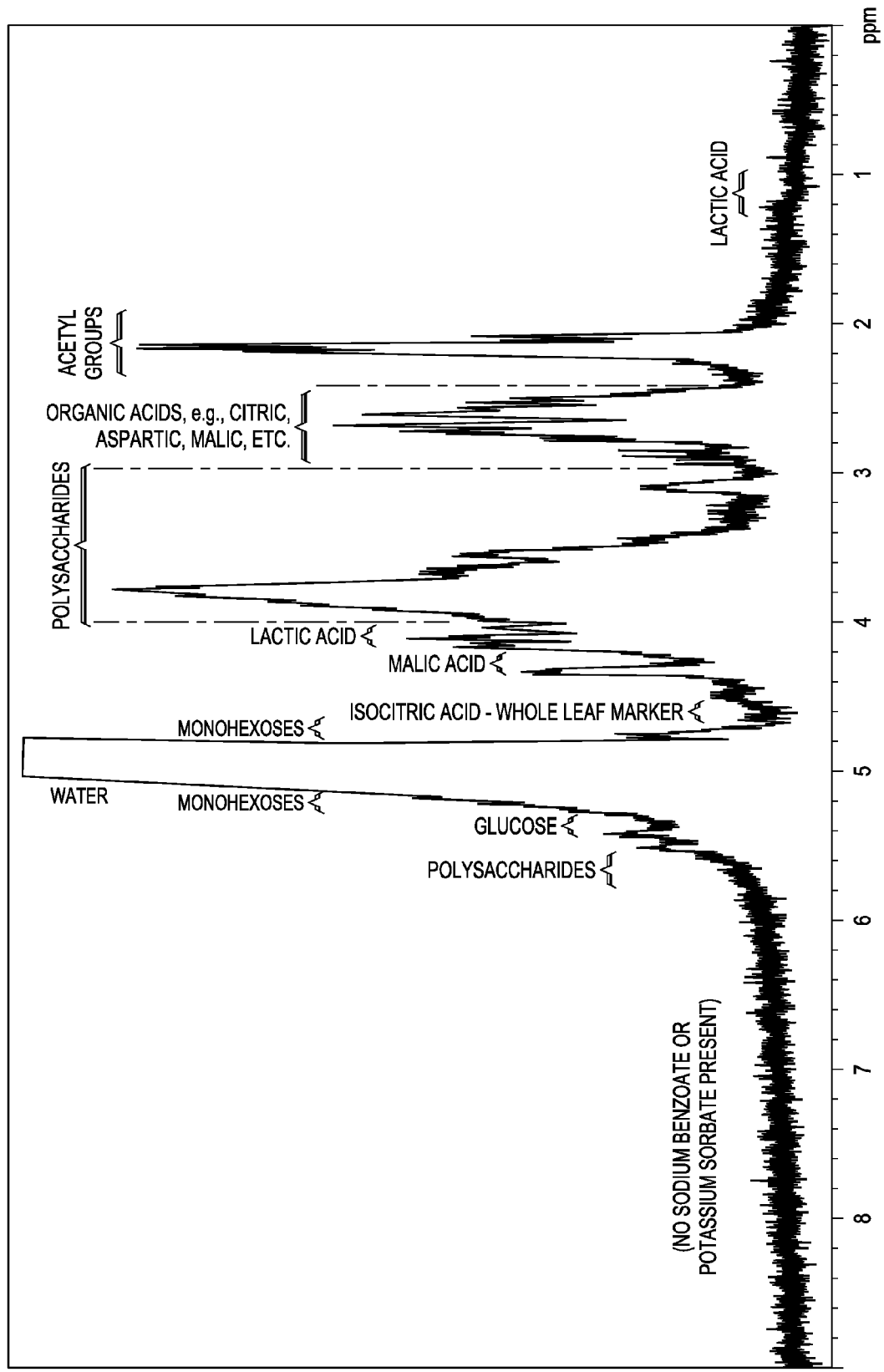

COMPOSITIONS AND METHODS OF ALOE POLYSACCHARIDES

CROSS-REFERENCE TO RELATED APPLICATIONS

This Non-Provisional patent application claims priority to U.S. Provisional Patent Application Ser. No. 61/294,970, filed on Jan. 14, 2010, the contents of which is incorporated by reference herein in their entirety.

STATEMENT OF FEDERALLY FUNDED RESEARCH

None.

SEQUENCE LISTING

Not Applicable.

INCORPORATION-BY-REFERENCE OF MATERIALS FILED ON COMPACT DISC

Not Applicable.

TECHNICAL FIELD OF THE INVENTION

The present invention relates in general to the field of *aloe* polysaccharides, and more particularly, to compositions of *aloe* polysaccharides and use of such compositions for as immunomodulators and for the treatment of different types of cancers.

BACKGROUND OF THE INVENTION

Without limiting the scope of the invention, its background is described in connection with compositions, methods of preparation, and therapeutic uses of *Aloe Vera* polysaccharides.

U.S. Pat. No. 7,196,072 issued to Pasco et al. (2007) describes a complex, water soluble polysaccharide fraction having potent immunostimulatory activity isolated from *Aloe vera*. The polysaccharide fraction has an apparent molecular weight above 2 million daltons with glucose, galactose, mannose and arabinose as its major components. The invention further describes pharmaceutical compositions containing the instant polysaccharide fraction, optionally in combination with acceptable pharmaceutical carriers and/or excipients. These pharmaceutical compositions may be used to provide immunostimulation to an individual in need of such treatment by administering to such an individual an effective amount of the composition.

U.S. Pat. No. 6,083,508 issued to Avalos and Danhof (2000) describes a process for forming an *aloe* product from only the leaf residue obtained after filleting *aloe* leaves having an internal fillet which is removed therefrom. According to the '508 patent the residue is formed into a slurry by grinding and the *aloe* product is generated from the slurry. In addition the steps of preparing the *aloe* product comprises cleansing an *aloe* leaf before filleting it, separating the slurry formed into a liquid and solids, and further treating the separated liquid to remove laxatives before forming the *aloe* product. Also, a process including all of the above steps may also be performed in order to form the liquid.

United States Patent Application No. 2006/0084629 (Needleman and Needleman, 2006) discloses a combination of two, specialized, high molecular weight-long chain fractions isolated from *Aloe Vera* and Maitake TD to stimulate immune system activity comprising long chain-high molecular weight polysaccharides which activate the body's natural immune response, triggering an increase in the production of macrophages, T-cells, B-cells, natural killer cells, cytokines and antibodies. These long chain polysaccharides together with other active ingredients may provide proper immune system support thereby preventing debilitating diseases such as cancer, heart disease and aging.

SUMMARY OF THE INVENTION

The present invention describes an *aloe* polysaccharide composition and the use of the composition as an immunomodulating agent and for the treatment of different types of cancers selected from leukemias and lymphomas, prostate cancer, breast cancer, and colon cancer, immune diseases, particularly immune related neoplasms.

The present invention provides a method for preparing a fine powder of a polymannan extract comprising the steps of: (i) weighing a specified quantity of a freeze-dried *aloe* powder, wherein the quantity is corrected for a moisture content, (ii) dissolving the freeze-dried *aloe* powder in deionized water to form a solution, (iii) adding an organic solvent to the solution to form a first mixture; wherein the organic solvent to the deionized water ratio is at least 2.5:1, (iv) allowing the first mixture to settle for at least 8 hours, (v) withdrawing a specified volume of a supernatant from the first mixture and adding an excess volume of the supernatant solution to form a second mixture, (vi) centrifuging the second mixture, (vii) observing for a presence of a precipitate in second mixture, (vii) adding an additional quantity of the organic solvent to first mixture if any precipitate is observed in second mixture, (viii) decanting the supernatant of first mixture by siphoning, wherein the decantation is done only if no precipitate is observed in second mixture, (ix) filtering the precipitate from first mixture by using a filter paper and a suction funnel under vacuum, (x) recovering the powder of the polymannan extract from the suction funnel by scraping, (xi) placing the powder of the polymannan extract in a capped lyophilization flask in a freezer for at least 8 hours, (xii) lyophilizing the frozen powder of the polymannan extract in a lyophilizer, and (xiii) grinding the lyophilized powder of the polymannan extract in a grinder to a very fine texture.

In one aspect the method further comprises the step of weighing, labeling, and storing the fine powder of the polymannan extract in a container. The freeze-dried *aloe* powder as described in the embodiment of the present invention is derived from an *Aloe* species selected from the group consisting of *Aloe vera, Aloe arborescens, Aloe aristata, Aloe dichotoma, Aloe nyeriensis, Aloe variegate, Aloe barbadensis,* and *Aloe wildii*. The freeze-dried *aloe* powder used in the present invention comprises *aloe* polysaccharides, wherein the *aloe* polysaccharides comprise one or more small chain, medium chain, large chain, very-large chain polysaccharides, or any combinations thereof. In a specific aspect the organic solvent is selected from the group consisting of methanol, ethanol, isopropyl alcohol, and propanol. In another aspect the *aloe* polysaccharides further comprise simple sugars, selected from the group consisting of glucose, mannose, arabinose, and galactose and have a molecular weight ranging from 11,500 Daltons to over 10,000,000 Daltons.

In another aspect the freeze-dried *aloe* powder has at least 25% of *aloe* polysaccharides. In yet another aspect the freeze-dried *aloe* powder has 25%, 30%, 40%, 50%, 60%, 70%, 80%, 90%, and 95% *aloe* polysaccharides. The freeze dried *aloe* powder as described in the method of the present invention comprises at least 14% of *aloe* polysaccharides having a molecular weight of 66,000 Daltons, at least 9% of *aloe* polysaccharides having a molecular weight of 480,000 Daltons, at least 3.5% of *aloe* polysaccharides having a molecular weight of 1,000,000 Daltons, at least 2.4% of *aloe* polysaccharides having a molecular weight of 2,000,000 Daltons.

In a specific aspect of the method relating to the *aloe* polysaccharide composition in the freeze dried *aloe* powder about 1.32%-6.36% of the *aloe* polysaccharides have a molecular weight of 2,000,000 Daltons, 2.55%-3.89% have a molecular weight of 1,000,000, and 63.85%-73.36% of *aloe* polysaccharides have a molecular weight of 480,000 Daltons. In one aspect the freeze dried *aloe* powder may contain one or more residual small molecular weight species, selected from the group consisting of glucose, organic acids, lactic acid, malic acids, citric acids, and aspartic acid. In another aspect the one or more residual small molecular weight species are present in amounts ranging from 14%-24%. In yet another aspect the fine powder of the polymannan extract is used on the preparation of a pharmaceutical composition to be used in the treatment of one or more malignacies selected from the group consisting of leukemias and lymphomas, prostate cancer, breast cancer, and colon cancer, and for the treatment of one or more immune disorders.

In another embodiment the present invention discloses a sterile injectable formulation of a polymannan extract comprising: a specified quantity of very fine polymannan extract dissolved in deionized water and one or more pharmaceutical preservatives. The one or more pharmaceutical preservatives the may be used in the formulation described hereinabove is selected from the group consisting of parabens, benzoic acid and their salts, mercurials, quarternary ammonium salts, benzyl alcohol and other related alcohols, and phenols. In a specific aspect the preservative is benzyl alcohol. In one aspect the polymannan extract comprises *aloe* polysaccharides, wherein the *aloe* polysaccharides comprise one or more small chain, medium chain, large chain, very-large chain polysaccharides, or any combinations thereof. In another aspect the *aloe* polysaccharides further comprise simple sugars, selected from the group consisting of glucose, mannose, arabinose, and galactose.

In other specific aspects the *aloe* polysaccharides have a molecular weight ranging from 11,500 Daltons to over 10,000,000 Daltons and the polymannan extract has at least 25% of *aloe* polysaccharides, wherein the polymannan extract has 25%, 30%, 40%, 50%, 60%, 70%, 80%, 90%, and 95% *aloe* polysaccharides. In a related aspect the polymannan extract comprises at least 14% of *aloe* polysaccharides having a molecular weight of 66,000 Daltons, at least 9% have a molecular weight of 480,000 Daltons, at least 3.5% have a molecular weight of 1,000,000 Daltons, and at least 2.4% of *aloe* polysaccharides having a molecular weight of 2,000,000 Daltons. The composition of the present invention is used in the treatment of one or more cancers selected from the group consisting of leukemias and lymphomas, prostate cancer, breast cancer, and colon cancer, for immunomodulation, immunostimulation, or for the treatment of an individual with a compromised immune system or an immune disease. The composition of the present invention causes a 75-80% increase in one or more natural killer (NK) cells.

In yet another embodiment the present invention describes a treatment for one or more cancers selected from the group consisting of leukemias and lymphomas, prostate cancer, breast cancer, and colon cancer, comprising the steps of: identifying an individual in need of treatment against the one or more cancers and injecting a sterile injectable polymannan extract formulation two to three times in a week in a dosage sufficient to treat the one or more cancers, wherein the sterile injectable polymannan extract formulation comprises a specified quantity of very fine polymannan extract dissolved in deionized water; and one or more pharmaceutical preservatives. The method further comprises the steps of: withdrawing blood samples from the individual at one or more specified intervals and measuring a level of a caspase 3 protein in the blood and comparing the level obtained with the level prior to the injection, wherein an increased level in caspase 3 is directly related to an increased level of apoptosis of the one or more cancer cells.

In one aspect the dosage of the sterile injectable polymannan extract formulation is dependent on a weight, an age, an ethnicity, and a gender of the individual. In another aspect the polymannan extract comprises *aloe* polysaccharides, wherein the *aloe* polysaccharides comprise one or more small chain, medium chain, large chain, very-large chain polysaccharides, or any combinations thereof. In yet another aspect the *aloe* polysaccharides have a molecular weight ranging from 11,500 Daltons to over 10,000,000 Daltons. The polymannan extract as described in the method of the present invention has at least 25% of *aloe* polysaccharides. The polymannan extract of the method of the present invention causes a 75-80% increase in one or more natural killer (NK) cells.

In one embodiment the present invention discloses a method of immunomodulation or immunostimulation in an individual with a compromised immune system or an immune disease comprising the steps of: (i) identifying the individual with the compromised immune system or an immune disease and in need of immunomodulation or immunostimulation, (ii) administering intravenously a specified dosage of a sterile injectable polymannan extract formulation, wherein the sterile injectable polymannan extract formulation comprises a specified quantity of very fine polymannan extract dissolved in deionized water; and one or more pharmaceutical preservatives, wherein the dosage of the sterile injectable polymannan extract formulation is dependent on a weight, an age, an ethnicity, and a gender of the individual, (iii) withdrawing blood samples from the individual at one or more specified intervals, and measuring a level of a tumor necrosis factor-alpha (TNFα) in the blood and comparing the level obtained with the level prior to the injection; wherein an increased level in the TNFα indicates immunomodulation or immunostimulation. In a specific aspect the immune disease is an immune related neoplasm. In one aspect the polymannan extract comprises *aloe* polysaccharides, wherein the *aloe* polysaccharides comprise one or more small chain, medium chain, large chain, very-large chain polysaccharides, or any combinations thereof. In another aspect the polymannan extract causes a 75-80% increase in one or more natural killer (NK) cells. In yet another aspect the polymannan extract has at least 25% of *aloe* polysaccharides.

BRIEF DESCRIPTION OF THE DRAWINGS

For a more complete understanding of the features and advantages of the present invention, reference is now made to the detailed description of the invention along with the accompanying figures and in which:

FIG. 4B is the proton-nuclear magnetic resonance profile of a methanol precipitated *aloe* polysaccharide concentrate;

FIG. 5B is the proton-nuclear magnetic resonance profile of a ethanol precipitated *aloe* polysaccharide concentrate;

FIG. 6B is the proton-nuclear magnetic resonance profile of an isopropyl alcohol precipitated *aloe* polysaccharide concentrate;

FIG. 7B is the proton-nuclear magnetic resonance profile of a propanol precipitated *aloe* polysaccharide concentrate.

DETAILED DESCRIPTION OF THE INVENTION

Figure 1:
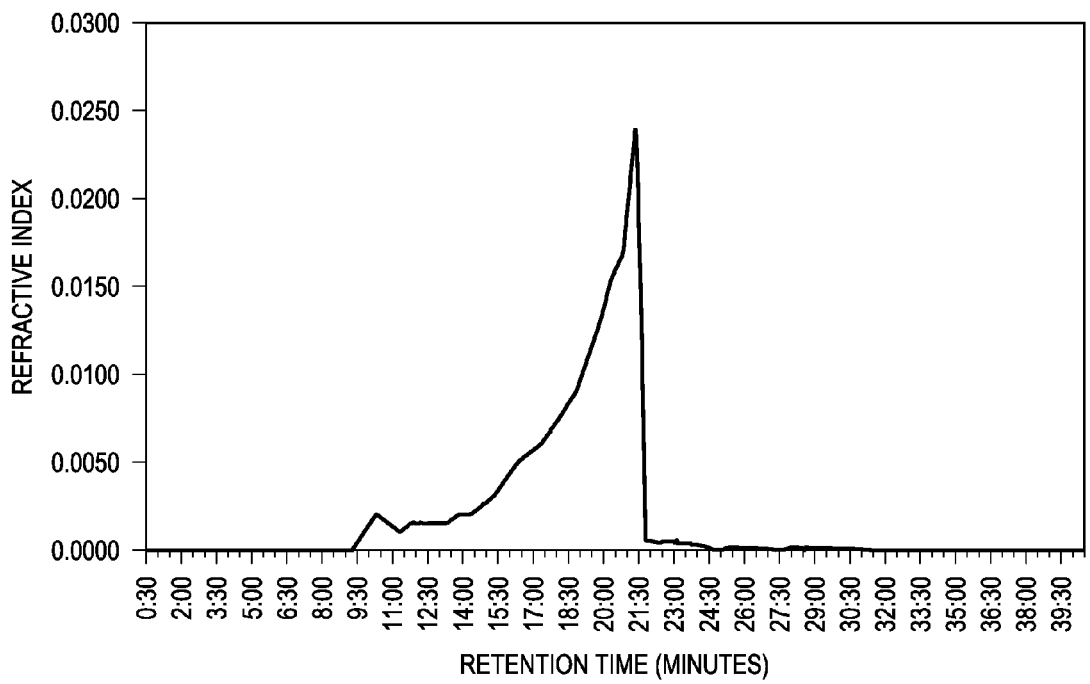
FIG. 1 shows a size-exclusion chromatogram of an *aloe* polysaccharide showing the retention times of the different glucose and mannose sub-units.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The present invention describes a process for preparing a polymannan extract and the use of the said extract in the form of an injection as an immune stimulatory compound. Immune stimulation is assessed using macrophages/monocytes of human origin and the cell type is assessed for the secretion of tumor necrosis factor alpha (TNFα).

*Aloe* polysaccharides are generally considered to be those molecules composed predominantly of glucose and mannose simple sugars having chain lengths of 10,000 Daltons to those with molecular weights of 10,000,000 Daltons. The higher the mannose content and longer the chain length the greater is the immunomodulatory activity expressed by the polysaccharides. The different long, unbranched chains comprising these *aloe* polysaccharides are listed in Table 1.

TABLE 1

*Aloe* polysaccharide compositions and pharmacological actions.

| | # of Sugar Residues | Mol. Wt (Daltons) | Pharmacological Actions |
| --- | --- | --- | --- |
| Small Chain Polysaccharides | 70-650 | 11,500->100,000 | Diabetes Tyrosinase inhibition (skin lightening) Anti-inflammatory activity (Cox-2 inhibition) |
| Medium Chain Polysaccharides | 1500 | 250,000 | Anti-oxidant Protects heart, lungs (emphysema), and nervous system (Parkinsonism) |
| Large Chain Polysaccharides | 4000-5000 | 650,000 | Antibacterial Induction of healing |
| Very Large Polysaccharides | 8000-9000 | 2,000,000-10,000,000 | Immunomodulatory activity Stimulation of β-lymphocytes with the elaboration of antibodies Increasing level of natural killer cells Release of large quantities of TNFα to cause angiogenesis in wounds and promotion of healing |

*Aloe* polysaccharides with molecular weights of 100,000 Daltons or more are listed in Table 2.

TABLE 2

Compositions and molecular weights of *aloe* polysaccharides having Mol. Wts of 100,000 or greater.

| | Mol. Wt (Daltons) | Major Components |
| --- | --- | --- |
| Aloeride | 2,000,000-10,000,000 | Arabinose, galactose, glucose, mannose |
| Acemannan | 900,000-1,500,000 | Glucose, mannose |
| Manapol | 500,000-900,000 | Glucose, mannose |
| Aloemannan | 100,000-500,000 | Glucose, Mannose |

The precursor material for the polymannan extract is described by the inventors in an previous patent (U.S. Pat. No. 6,083,508—Avalos and Danhof, 2000) titled "Method of Processing *Aloe* Leaves". The certificate of analysis of the polymannan extract precursor material is presented in Table 3.

Figure 2:
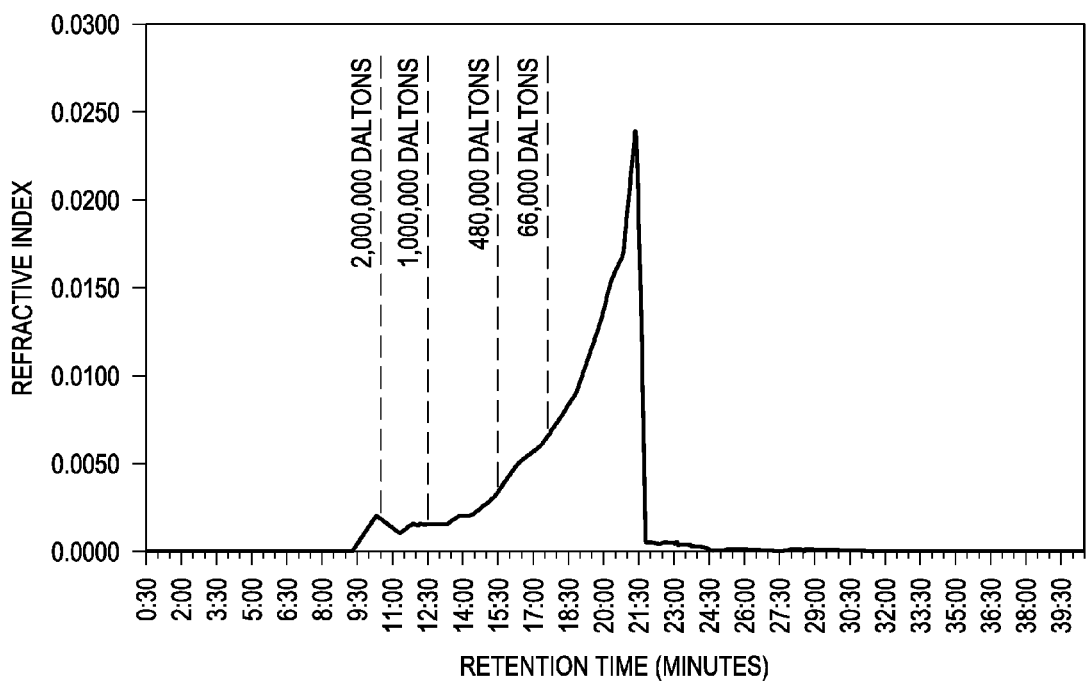
FIG. 2 shows the size-exclusion chromatogram of an *aloe* polysaccharide showing the peaks corresponding to the different glucose and mannose sub-units.
Figure 3:
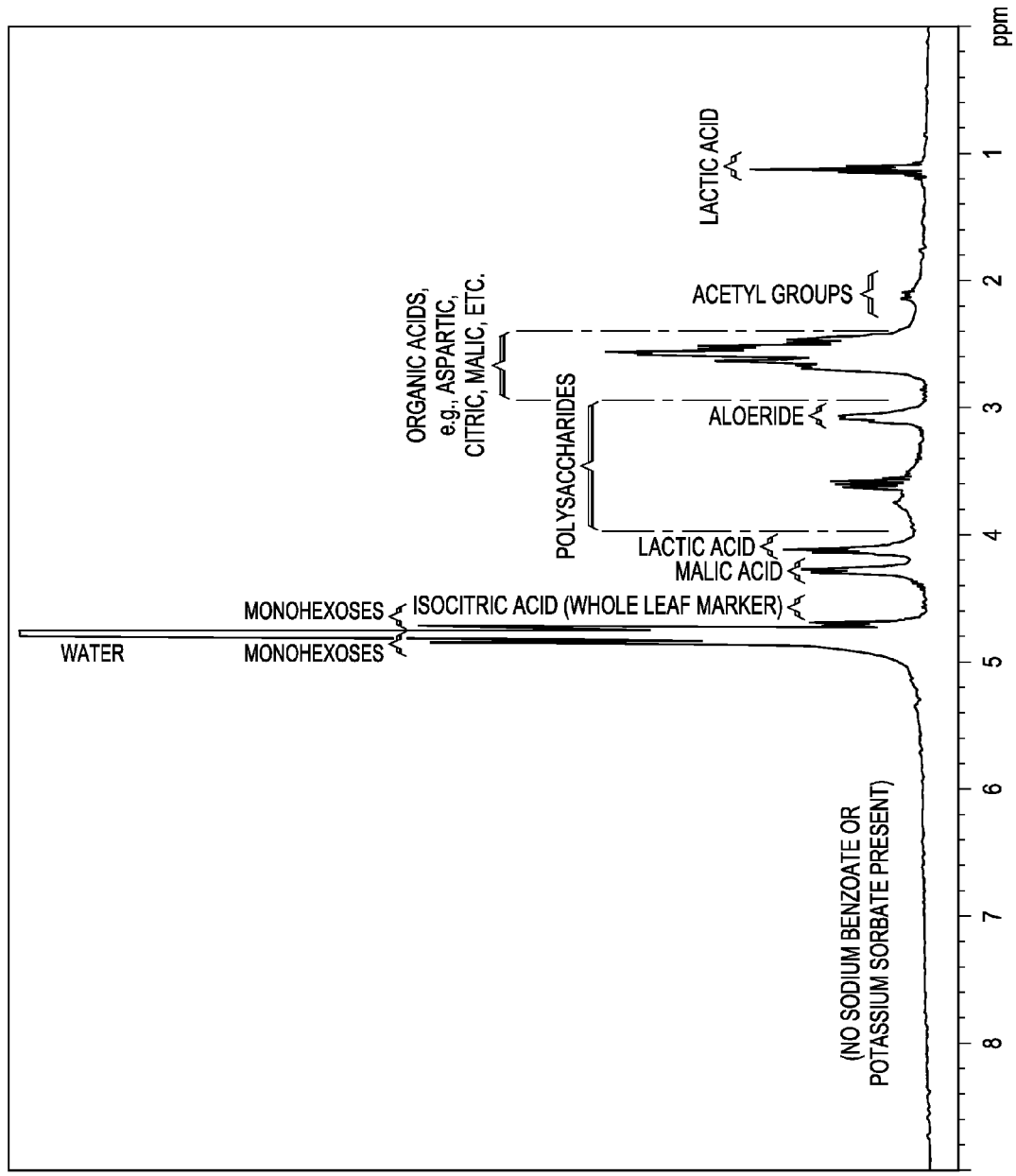
FIG. 3 is the proton-nuclear magnetic resonance profile of the polymannan extract of the present invention.
Figure 4A:
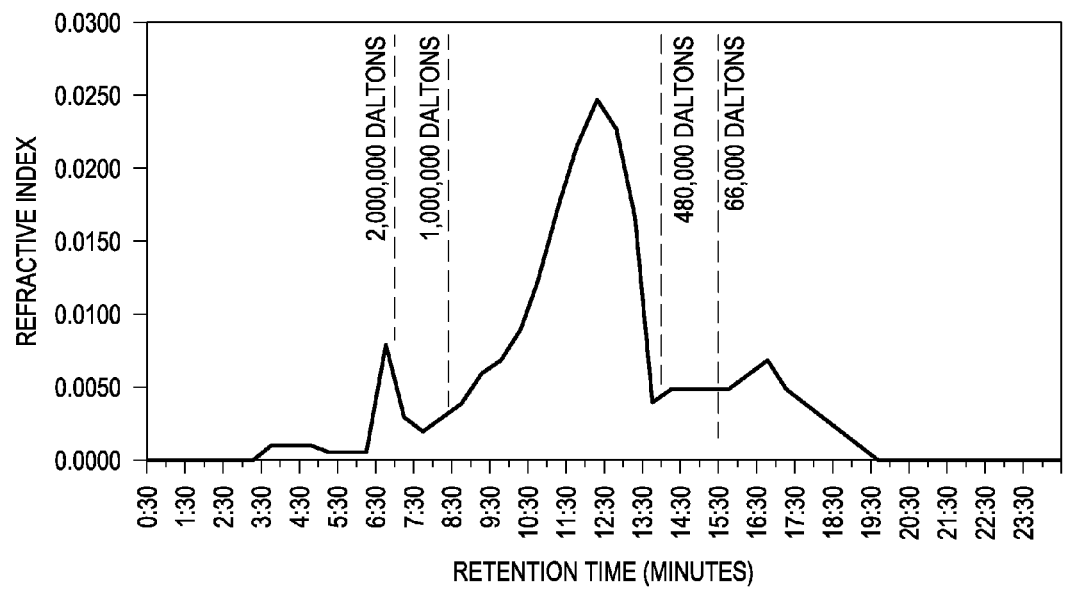
FIG. 4A is a HPLC chromatogram showing the amounts of polysaccharide in each polysaccharide molecular group in a methanol precipitated *aloe* polysaccharide concentrate.
Figure 5A:
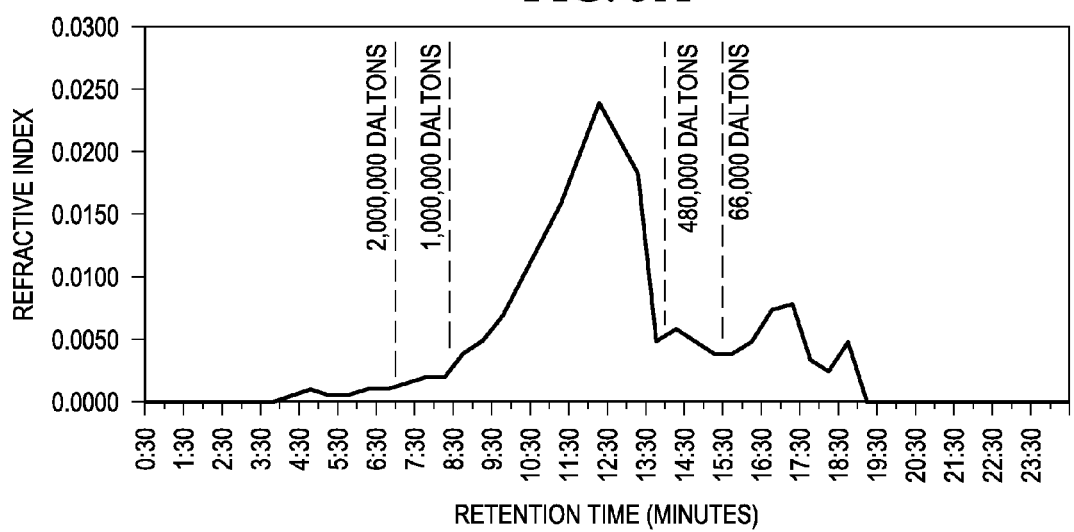
FIG. 5A is a HPLC chromatogram showing the amounts of polysaccharide in each polysaccharide molecular group in a ethanol precipitated *aloe* polysaccharide concentrate.
Figure 6A:
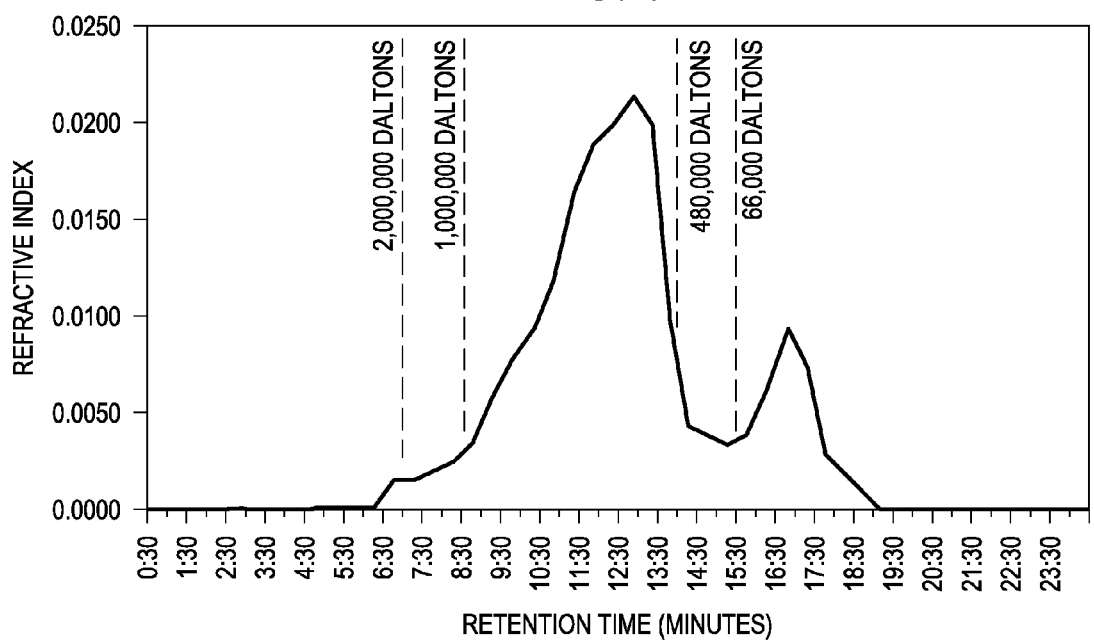
FIG. 6A is a HPLC chromatogram showing the amounts of polysaccharide in each polysaccharide molecular group in an isopropyl alcohol precipitated *aloe* polysaccharide concentrate.
Figure 7A:
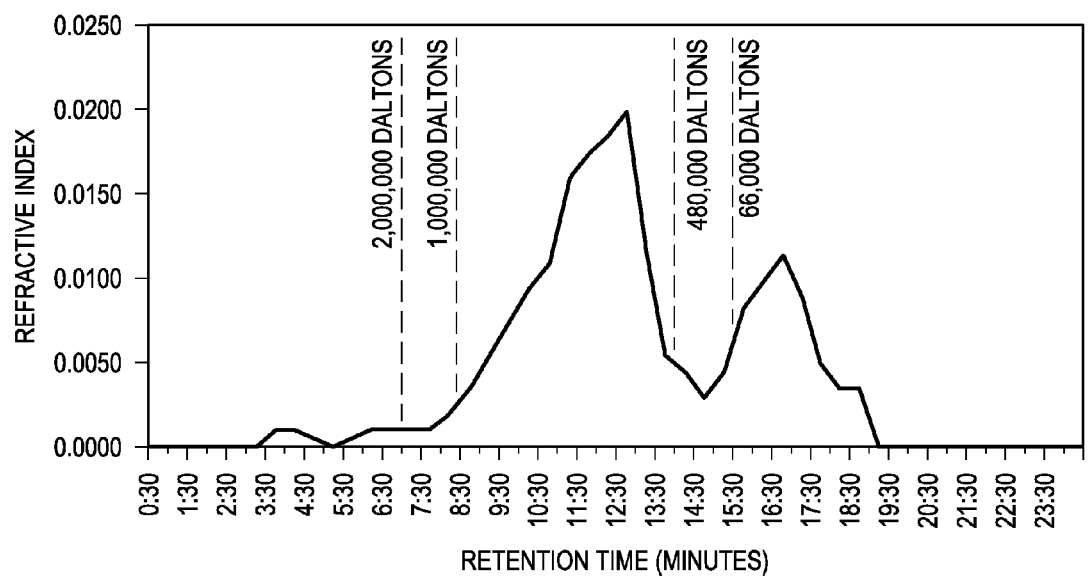
FIG. 7A is a HPLC chromatogram showing the amounts of polysaccharide in each polysaccharide molecular group in a propanol precipitated *aloe* polysaccharide concentrate.

FIG. 1 is a size-exclusion chromatogram of an *aloe* polysaccharide preparation showing retention times of various-sized glucose and mannose subunits. FIG. 2 is a size-exclusion chromatogram of an *aloe* polysaccharide preparation identifying molecular weights ranging from 100 to 10,000,000 Daltons. FIG. 3 is the proton-nuclear magnetic resonance profile of the polymannan extract of the present invention. FIG. 3 shows: (i) the absence of the standard preservatives—sodium benzoate and potassium sorbate, (ii) the presence of smaller monohexoses, (iii) the peaks of isocitric acid indicating a whole leaf methodology was employed in processing the raw *aloe* material, (iv) the presence of malic acid peaks—a primary marker for *Aloe vera*, (v) the presence of the aloeride/acemannan peak in the polysaccharide portion of the profile confirming the presence of the large polysaccharide species, and (vi) acetyl groups are present confirming the presence of the partially acetylated polysaccharide glucomannans.

Size exclusion chromatography (SEC) of an *aloe* preparation prior to polymannan extraction:

Equipment: HPLC system is a Hitachi L-7100 pump and 7250 autosampler paired to a Waters 410 differential refractometer. The SEC is a Tosoh Biosep G6000 PWXL TSK Gel 30 cm×7.8 mm operated in a column heater at 70° C. Molecular weight standards are from Sigma—2,000,000 Daltons, 1,000,000 Daltons, 480,000 Daltons, 66,000 Daltons, and 180 Daltons (glucose). The mobile phase is de-ionized water with flow rate of 0.70 mL/min. The injection volume is 10 uL. The SEC method is described by Pugh et al. (2001).

TABLE 3

Certificate of analysis of Polymannan Extract Precursor Material.

| Parameter | Constituent Range | Determined Value | Assessment |
|---|---|---|---|
| Powder: | | | |
| Color: | White to light tan | Offwhite | Complies |
| Characteristics: | Finely granular | Finely granular | Complies |
| Rheology: | Free-flowing | Free-flowing | Complies |
| Taste: | Salty | Salty | Complies |
| Iodine test: | Negative | Negative | Complies |
| Moisture: | 2.2-7.0% | 3.70% | Complies |
| Solubility: | Complete | Complete | Complies |
| Minerals: | | | |
| $Ca^{++}$ | >25 mg/gram | 56.3 mg/gram | Complies |
| $Mg^{++}$ | >10 mg/gram | 14.3 mg/gram | Complies |
| Organic Acids: | | | |
| Citric: | Present | Present | Complies |
| Isocitric: | Present | Present | Complies |
| Lactic: | <25 mg/gram | 12 ppm | Complies |
| Malic: | >250 mg/gram | 410 mg/gram | Complies |
| Anthraquinones: | | | |
| Aloin A: | <0.05 ppm | 0.02 ppm | Complies |
| Aloin B: | <0.03 ppm | 0.01 ppm | Complies |
| Aloe-emodin: | <0.02 ppm | 0.005 ppm | Complies |
| Emodin: | <0.01 ppm | 0.001 ppm | Complies |
| Brix Value: | <1.0 | Negative | Complies |

TABLE 4

SEC results for *aloe* preparation prior to polymannan extraction.
*Aloe* #09116

| Refraction Time | Refractive Index | Area | Σ Area | % Area | Molecular Size |
|---|---|---|---|---|---|
| 0:30 | 0.0000 | 0.0000 | | | |
| 1:00 | 0.0000 | 0.0000 | | | |
| 1:30 | 0.0000 | 0.0000 | | | |
| 2:00 | 0.0000 | 0.0000 | | | |
| 2:30 | 0.0000 | 0.0000 | | | |
| 3:00 | 0.0000 | 0.0000 | | | |
| 3:30 | 0.0000 | 0.0000 | | | |
| 4:00 | 0.0000 | 0.0000 | | | |
| 4:30 | 0.0000 | 0.0000 | | | |
| 5:00 | 0.0000 | 0.0000 | | | |
| 5:30 | 0.0000 | 0.0000 | | | |
| 6:00 | 0.0000 | 0.0000 | | | |
| 6:30 | 0.0000 | 0.0000 | | | |
| 7:00 | 0.0000 | 0.0000 | | | |
| 7:30 | 0.0000 | 0.0000 | | | |
| 8:00 | 0.0000 | 0.0000 | | | |
| 8:30 | 0.0000 | 0.0000 | | | |
| 9:00 | 0.0000 | 0.0000 | | | |
| 9:30 | 0.0010 | 0.0014 | | | |
| 10:00 | 0.0020 | 0.0046 | | | |
| 10:30 | 0.0015 | 0.0058 | 0.012 | 2.44% | $2 \times 10^6$ |
| 11:00 | 0.0010 | 0.0042 | | | |
| 11:30 | 0.0015 | 0.0039 | | | |
| 12:00 | 0.0015 | 0.0049 | | | |
| 12:30 | 0.0015 | 0.0049 | 0.018 | 3.69% | $1 \times 10^6$ |
| 13:00 | 0.0015 | 0.0049 | | | |
| 13:30 | 0.0020 | 0.0056 | | | |
| 14:00 | 0.0020 | 0.0065 | | | |
| 14:30 | 0.0025 | 0.0072 | | | |
| 15:00 | 0.0030 | 0.0088 | | | |
| 15:30 | 0.0040 | 0.0111 | 0.044 | 9.09% | $4.80 \times 10^5$ |
| 16:00 | 0.0050 | 0.0144 | | | |
| 16:30 | 0.0055 | 0.0169 | | | |
| 17:00 | 0.0060 | 0.0186 | | | |
| 17:30 | 0.0070 | 0.0209 | 0.071 | 14.59% | $6.6 \times 10^4$ |
| 18:00 | 0.0080 | 0.0241 | | | |
| 18:30 | 0.0090 | 0.0274 | | | |
| 19:00 | 0.0110 | 0.0320 | | | |
| 19:30 | 0.0130 | 0.0385 | | | |
| 20:00 | 0.0155 | 0.0457 | | | |
| 20:30 | 0.0170 | 0.0524 | | | |
| 21:00 | 0.0240 | 0.0649 | | | |
| 21:30 | 0.0005 | 0.0457 | | | |
| 22:00 | 0.0004 | 0.0015 | | | |
| 22:30 | 0.0005 | 0.0014 | | | |
| 23:00 | 0.0004 | 0.0015 | | | |
| 23:30 | 0.0003 | 0.0012 | | | |
| 24:00 | 0.0000 | 0.0000 | 0.340 | 70.20% | |
| | 0.0000 | 0.4849 | | 100.00% | |

*Aloe* Precipitant Evaluation Study:

25 ml samples of COATS concentrated *aloe* were pipetted into 200 ml beakers and 125 ml of various polysaccharide precipitant liquids were added to the beaker and thoroughly stirred. The precipitated polysaccharides were collected by filtration through tared dehydrated filter papers which, following filtration, were placed in the drying oven overnight. The next morning the dry weight of the precipitated polysaccharide was determined. The inventors studied four alcoholic precipitants were studied including, methanol, ethanol, isopropyl alcohol, and propanol. The powders were passed through a HPLC procedure which determined the various quantities of all of the molecular species which was recorded with determination of the amounts of polysaccharides in each of the polysaccharide molecular groups, including greater than 2,000,000 Daltons, greater than 1,000,000 Daltons, greater than 480,000 Daltons, greater than 66,000 Daltons, and the residual fraction containing the very small molecular species, e.g. glucose having a M.W. of 180. (HPLC data shown in Tables 6-9). The HPLC chromatograms corresponding to the four precipitants methanol, ethanol, isopropyl alcohol, and propanol is shown in FIGS. 4A, 5A, 6A, and 7A, respectively. Proton Nuclear Magnetic Resonance Profiles of the precipitates were also obtained and are shown in FIGS. 4B, 5B, 6B, and 7B. The data collected is shown in Table 5.

TABLE 5

Data from the *aloe* precipitant evaluation study.

| Precipitant | M.W. $2.0 \times 10^6$ | M.W. $1.0 \times 10^6$ | M.W. $4.8 \times 10^5$ | M.W. $6.6 \times 10^4$ | M.W. Residual |
|---|---|---|---|---|---|
| METHANOL | 6.36% | 3.89% | 68.56% | 6.92% | 14.27% |
| ETHANOL | 2.52% | 3.21% | 70.70% | 6.94% | 16.57% |
| ISOPROPYL ALCOHOL | 1.32% | 3.43% | 73.36% | 5.91% | 15.99% |
| PROPANOL | 2.74% | 2.55% | 63.85% | 6.92% | 23.94% |

TABLE 6

HPLC data showing the amounts of polysaccharide in each polysaccharide molecular group in a methanol precipitated *aloe* polysaccharide concentrate.
*Aloe* #09423-A

| Retention Time | Refractive Index | Area | Σ Area | % Area | Molecular Size |
|---|---|---|---|---|---|
| 0:30 | 0.0000 | 0.0000 | | | |
| 1:00 | 0.0000 | 0.0000 | | | |
| 1:30 | 0.0000 | 0.0000 | | | |
| 2:00 | 0.0000 | 0.0000 | | | |
| 2:30 | 0.0000 | 0.0000 | | | |
| 3:00 | 0.0000 | 0.0000 | | | |
| 3:30 | 0.0010 | 0.0014 | | | |
| 4:00 | 0.0010 | 0.0033 | | | |
| 4:30 | 0.0010 | 0.0033 | | | |
| 5:00 | 0.0005 | 0.0026 | | | |
| 5:30 | 0.0005 | 0.0016 | | | |
| 6:00 | 0.0005 | 0.0016 | | | |
| 6:30 | 0.0080 | 0.0119 | | | |
| 7:00 | 0.0030 | 0.0191 | 0.045 | 6.36% | $2 \times 10^6$ |
| 7:30 | 0.0020 | 0.0084 | | | |
| 8:00 | 0.0030 | 0.0079 | | | |
| 8:30 | 0.0040 | 0.0111 | 0.027 | 3.89% | $1 \times 10^6$ |
| 9:00 | 0.0060 | 0.0158 | | | |
| 9:30 | 0.0070 | 0.0209 | | | |
| 10:00 | 0.0090 | 0.0255 | | | |
| 10:30 | 0.0130 | 0.0348 | | | |
| 11:00 | 0.0180 | 0.0491 | | | |
| 11:30 | 0.0220 | 0.0640 | | | |
| 12:00 | 0.0250 | 0.0756 | | | |
| 12:30 | 0.0230 | 0.0785 | | | |
| 13:00 | 0.0170 | 0.0665 | | | |
| 13:30 | 0.0040 | 0.0374 | | | |
| 14:00 | 0.0050 | 0.0144 | 0.482 | 68.56% | $4.80 \times 10^5$ |
| 14:30 | 0.0050 | 0.0163 | | | |
| 15:00 | 0.0050 | 0.0163 | | | |
| 15:30 | 0.0050 | 0.0163 | 0.049 | 6.93% | $6.6 \times 10^4$ |
| 16:00 | 0.0060 | 0.0176 | | | |
| 16:30 | 0.0070 | 0.0209 | | | |
| 17:00 | 0.0050 | 0.0200 | | | |
| 17:30 | 0.0040 | 0.0149 | | | |
| 18:00 | 0.0030 | 0.0116 | | | |
| 18:30 | 0.0020 | 0.0084 | | | |
| 19:00 | 0.0010 | 0.0051 | | | |
| 19:30 | 0.0000 | 0.0019 | | | |
| 20:00 | 0.0000 | 0.0000 | | | |
| 20:30 | 0.0000 | 0.0000 | | | |
| 21:00 | 0.0000 | 0.0000 | | | |
| 21:30 | 0.0000 | 0.0000 | | | |
| 22:00 | 0.0000 | 0.0000 | | | |
| 22:30 | 0.0000 | 0.0000 | | | |
| 23:00 | 0.0000 | 0.0000 | | | |
| 23:30 | 0.0000 | 0.0000 | | | |
| 24:00 | 0.0000 | 0.0000 | 0.100 | 14.27% | |
| | 0.0000 | 0.7036 | | 100.00% | |

TABLE 7

HPLC data showing the amounts of polysaccharide in each polysaccharide molecular group in an ethanol precipitated *aloe* polysaccharide concentrate.
*Aloe* #09423-B

| Retention Time | Refractive Index | Area | Σ Area | % Area | Molecular Size |
|---|---|---|---|---|---|
| 0:30 | 0.0000 | 0.0000 | | | |
| 1:00 | 0.0000 | 0.0000 | | | |
| 1:30 | 0.0000 | 0.0000 | | | |
| 2:00 | 0.0000 | 0.0000 | | | |
| 2:30 | 0.0000 | 0.0000 | | | |
| 3:00 | 0.0000 | 0.0000 | | | |
| 3:30 | 0.0000 | 0.0000 | | | |
| 4:00 | 0.0005 | 0.0007 | | | |
| 4:30 | 0.0010 | 0.0023 | | | |
| 5:00 | 0.0005 | 0.0026 | | | |
| 5:30 | 0.0005 | 0.0016 | | | |
| 6:00 | 0.0010 | 0.0023 | | | |
| 6:30 | 0.0010 | 0.0033 | | | |
| 7:00 | 0.0015 | 0.0039 | 0.017 | 2.52% | $2 \times 10^6$ |
| 7:30 | 0.0020 | 0.0056 | | | |
| 8:00 | 0.0020 | 0.0065 | | | |
| 8:30 | 0.0040 | 0.0093 | 0.021 | 3.21% | $1 \times 10^6$ |
| 9:00 | 0.0050 | 0.0144 | | | |
| 9:30 | 0.0070 | 0.0190 | | | |
| 10:00 | 0.0100 | 0.0269 | | | |
| 10:30 | 0.0130 | 0.0366 | | | |
| 11:00 | 0.0160 | 0.0464 | | | |
| 11:30 | 0.0200 | 0.0575 | | | |
| 12:00 | 0.0240 | 0.0705 | | | |
| 12:30 | 0.0210 | 0.0739 | | | |
| 13:00 | 0.0185 | 0.0648 | | | |
| 13:30 | 0.0050 | 0.0416 | | | |
| 14:00 | 0.0060 | 0.0176 | 0.469 | 70.76% | $4.80 \times 10^5$ |
| 14:30 | 0.0050 | 0.0181 | | | |
| 15:00 | 0.0040 | 0.0149 | | | |
| 15:30 | 0.0040 | 0.0130 | 0.046 | 6.94% | $6.6 \times 10^4$ |
| 16:00 | 0.0050 | 0.0144 | | | |
| 16:30 | 0.0075 | 0.0197 | | | |
| 17:00 | 0.0080 | 0.0251 | | | |
| 17:30 | 0.0035 | 0.0198 | | | |
| 18:00 | 0.0025 | 0.0100 | | | |
| 18:30 | 0.0050 | 0.0116 | | | |
| 19:00 | 0.0000 | 0.0094 | | | |
| 19:30 | 0.0000 | 0.0000 | | | |
| 20:00 | 0.0000 | 0.0000 | | | |
| 20:30 | 0.0000 | 0.0000 | | | |
| 21:00 | 0.0000 | 0.0000 | | | |
| 21:30 | 0.0000 | 0.0000 | | | |
| 22:00 | 0.0000 | 0.0000 | | | |
| 22:30 | 0.0000 | 0.0000 | | | |
| 23:00 | 0.0000 | 0.0000 | | | |
| 23:30 | 0.0000 | 0.0000 | | | |
| 24:00 | 0.0000 | 0.0000 | 0.110 | 16.57% | |
| | 0.0000 | 0.6630 | | 100.00% | |

TABLE 8

HPLC data showing the amounts of polysaccharide in each polysaccharide molecular group in an isopropyl alcohol precipitated *aloe* polysaccharide concentrate.
*Aloe* #09423-C

| Retention Time | Refractive Index | Area | Σ Area | % Area | Molecular Size |
|---|---|---|---|---|---|
| 0:30 | 0.0000 | 0.0000 | | | |
| 1:00 | 0.0000 | 0.0000 | | | |
| 1:30 | 0.0000 | 0.0000 | | | |
| 2:00 | 0.0000 | 0.0000 | | | |
| 2:30 | 0.0001 | 0.0001 | | | |
| 3:00 | 0.0000 | 0.0002 | | | |

TABLE 8-continued

HPLC data showing the amounts of polysaccharide in each polysaccharide molecular group in an isopropyl alcohol precipitated *aloe* polysaccharide concentrate.

Aloe #09423-C

| Retention Time | Refractive Index | Area | Σ Area | % Area | Molecular Size |
|---|---|---|---|---|---|
| 3:30 | 0.0000 | 0.0000 | | | |
| 4:00 | 0.0000 | 0.0000 | | | |
| 4:30 | 0.0001 | 0.0001 | | | |
| 5:00 | 0.0001 | 0.0003 | | | |
| 5:30 | 0.0001 | 0.0003 | | | |
| 6:00 | 0.0001 | 0.0003 | | | |
| 6:30 | 0.0015 | 0.0023 | | | |
| 7:00 | 0.0015 | 0.0049 | 0.009 | 1.32% | $2 \times 10^6$ |
| 7:30 | 0.0020 | 0.0056 | | | |
| 8:00 | 0.0025 | 0.0072 | | | |
| 8:30 | 0.0035 | 0.0095 | 0.022 | 3.43% | $1 \times 10^6$ |
| 9:00 | 0.0060 | 0.0148 | | | |
| 9:30 | 0.0080 | 0.0223 | | | |
| 10:00 | 0.0095 | 0.0281 | | | |
| 10:30 | 0.0120 | 0.0343 | | | |
| 11:00 | 0.0165 | 0.0452 | | | |
| 11:30 | 0.0190 | 0.0571 | | | |
| 12:00 | 0.0200 | 0.0631 | | | |
| 12:30 | 0.0215 | 0.0671 | | | |
| 13:00 | 0.0200 | 0.0678 | | | |
| 13:30 | 0.0100 | 0.0513 | | | |
| 14:00 | 0.0045 | 0.0249 | 0.476 | 73.36% | $4.80 \times 10^5$ |
| 14:30 | 0.0040 | 0.0139 | | | |
| 15:00 | 0.0035 | 0.0123 | | | |
| 15:30 | 0.0040 | 0.0121 | 0.038 | 5.91% | $6.6 \times 10^4$ |
| 16:00 | 0.0065 | 0.0164 | | | |
| 16:30 | 0.0096 | 0.0254 | | | |
| 17:00 | 0.0075 | 0.0283 | | | |
| 17:30 | 0.0030 | 0.0182 | | | |
| 18:00 | 0.0020 | 0.0084 | | | |
| 18:30 | 0.0010 | 0.0051 | | | |
| 19:00 | 0.0000 | 0.0019 | | | |
| 19:30 | 0.0000 | 0.0000 | | | |
| 20:00 | 0.0000 | 0.0000 | | | |
| 20:30 | 0.0000 | 0.0000 | | | |
| 21:00 | 0.0000 | 0.0000 | | | |
| 21:30 | 0.0000 | 0.0000 | | | |
| 22:00 | 0.0000 | 0.0000 | | | |
| 22:30 | 0.0000 | 0.0000 | | | |
| 23:00 | 0.0000 | 0.0000 | | | |
| 23:30 | 0.0000 | 0.0000 | | | |
| 24:00 | 0.0000 | 0.0000 | 0.104 | 15.99% | |
| | 0.0000 | 0.6487 | | 100.00% | |

TABLE 9

HPLC data showing the amounts of polysaccharide in each polysaccharide molecular group in a propanol precipitated *aloe* polysaccharide concentrate.

Aloe #09423-C

| Retention Time | Refractive Index | Area | Σ Area | % Area | Molecular Size |
|---|---|---|---|---|---|
| 0:30 | 0.0000 | 0.0000 | | | |
| 1:00 | 0.0000 | 0.0000 | | | |
| 1:30 | 0.0000 | 0.0000 | | | |
| 2:00 | 0.0000 | 0.0000 | | | |
| 2:30 | 0.0001 | 0.0001 | | | |
| 3:00 | 0.0000 | 0.0002 | | | |
| 3:30 | 0.0000 | 0.0000 | | | |
| 4:00 | 0.0000 | 0.0000 | | | |
| 4:30 | 0.0001 | 0.0001 | | | |
| 5:00 | 0.0001 | 0.0003 | | | |
| 5:30 | 0.0001 | 0.0003 | | | |
| 6:00 | 0.0001 | 0.0003 | | | |
| 6:30 | 0.0015 | 0.0023 | | | |
| 7:00 | 0.0015 | 0.0049 | 0.009 | 1.32% | $2 \times 10^6$ |
| 7:30 | 0.0020 | 0.0056 | | | |
| 8:00 | 0.0025 | 0.0072 | | | |
| 8:30 | 0.0035 | 0.0095 | 0.022 | 3.43% | $1 \times 10^6$ |
| 9:00 | 0.0060 | 0.0148 | | | |
| 9:30 | 0.0080 | 0.0223 | | | |
| 10:00 | 0.0095 | 0.0281 | | | |
| 10:30 | 0.0120 | 0.0343 | | | |
| 11:00 | 0.0165 | 0.0452 | | | |
| 11:30 | 0.0190 | 0.0571 | | | |
| 12:00 | 0.0200 | 0.0631 | | | |
| 12:30 | 0.0215 | 0.0671 | | | |
| 13:00 | 0.0200 | 0.0678 | | | |
| 13:30 | 0.0100 | 0.0513 | | | |
| 14:00 | 0.0045 | 0.0249 | 0.476 | 73.36% | $4.80 \times 10^5$ |
| 14:30 | 0.0040 | 0.0139 | | | |
| 15:00 | 0.0035 | 0.0123 | | | |
| 15:30 | 0.0040 | 0.0121 | 0.038 | 5.91% | $6.6 \times 10^4$ |
| 16:00 | 0.0065 | 0.0164 | | | |
| 16:30 | 0.0096 | 0.0254 | | | |
| 17:00 | 0.0075 | 0.0283 | | | |
| 17:30 | 0.0030 | 0.0182 | | | |
| 18:00 | 0.0020 | 0.0084 | | | |
| 18:30 | 0.0010 | 0.0051 | | | |
| 19:00 | 0.0000 | 0.0019 | | | |
| 19:30 | 0.0000 | 0.0000 | | | |
| 20:00 | 0.0000 | 0.0000 | | | |
| 20:30 | 0.0000 | 0.0000 | | | |
| 21:00 | 0.0000 | 0.0000 | | | |
| 21:30 | 0.0000 | 0.0000 | | | |
| 22:00 | 0.0000 | 0.0000 | | | |
| 22:30 | 0.0000 | 0.0000 | | | |
| 23:00 | 0.0000 | 0.0000 | | | |
| 23:30 | 0.0000 | 0.0000 | | | |
| 24:00 | 0.0000 | 0.0000 | 0.104 | 15.99% | |
| | 0.0000 | 0.6487 | | 100.00% | |

The polymannan extract is prepared by precipitation. The freeze dried *aloe* powder is described above was weighed after correcting appropriately for the moisture content. For example, if the moisture content is 3.7% and we need 80 gms, the inventors weighed out 82.96 gms (80 gms+(3.7%×80) gms). The weighed *aloe* powder was dissolved completely in one gallon of deionized water (D.I) in a stainless steel precipitation vessel. 2.5 gallons of 95% ethanol was added and stirred to ensure complete mixing. The vessel was covered with a stainless steel lid and the mixture was allowed to settle overnight.

The following day a 2 ml of clear supernatant was taken and 5 mL of 95% ethanol was added and the sample was centrifuged at 3000 rpm for 20 minutes. The sample was examined for precipitation, if no precipitate was observed then the precipitation was considered complete. If any significant degree of precipitation was observed then additional 95% ethanol was added to the precipitation vessel before proceeding. The clear supernatant fluid in the precipitation vessel was decanted by siphoning without disturbing the precipitate at the bottom of the vessel. The white precipitate at the bottom was separated by using a suction funnel (Whatman No. 42® quantitative ashless filter paper. The precipitated material was removed by scraping it into a 600 ml Virtis lyophilization flask, and by distributing the material over one side of the flask to form a thin layer with a large exposed surface area. The lyophilization flask was placed in a shell-freezer overnight. The next day the chilled lyophilization flask with its frozen contents, was placed on a lyophilizer operating at −90° C. and at ⅓ atmosphere for 24 hours. The lyophizer was turned off and the lyophilized powder was placed into a small powder grinder until it reduced to an evenly ground fine powder. The ground powder was weighed and placed in plastic small containers and the containers were stored in a freezer.

Preparation of an Injectable Solution of Polymannan Extract:

The polymannan extract powder (PME) prepared as described above was weighed (1.5 gms) after correcting for moisture content and having an aloeride content of at least 2% as determined by size exclusion chromatography. To 125 ml of warm D.I water 1 ml of concentrated HCl was added and stirred followed by the slow addition of the PME powder with constant stirring. The stirring was continued till all the PME powder dissolved and the solution was clear and colorless an additional amount of concentrated HCl was added to obtain a pH of 1.6 to 1.7 (measured continuously using a pH meter). Additional D.I water was added to adjust the volume to 150 ml followed by a pH monitoring to ensure a pH of 1.6-1.7. The PME solution was then poured into a Corning® 150 ml filter system flask with a pore size of 0.45 μm. The flask system was placed in a refrigerator and the filtrate was transferred to a Corning® 150 ml filter system flask with a pore size of 0.22 μm and placed in a refrigerator overnight. Under sterile conditions the filter top of the filter system was removed and the bottle was sealed with a sterile cap. The bottles were them transferred to a compounding lab, and under a sterile hood 0.9% benzyl alcohol was added as a preservative (because the final product is for multi-dosage use), and the solution was placed in sterile 10 mL glass vials and sealed with a multi-dosage closure. The vials are labeled with a batch number, control number, manufacturing date, expiration date of 6 months along with the names of the physician and patient.

PME Immunomodulatory Activity Assessment:

The immune stimulatory activity is assessed using macrophages/monocytes of human origin obtained from the American Type Culture Collection (ATCC) in Maryland. The cell type was assessed for the secretion of TNFα. Under standard cell conditions a small amount of the final PME product was introduced in the culture. Samples were drawn at 6, 12, and 24 hours and assessed for TNFα levels. A specific quantity of TNFα was not used because of the variability in the different cell batches. In a clinical setting the immunomodulatory response is expected to vary due to changing hemotological factors like the total leukocyte count, differential macrophage/monocyte count, number of surface mannose receptors on the white cells, amount of mannose-binding carrier protein, etc.

The white blood cell profile varies with cells constantly entering and leaving the blood stream. The affinity of the cellular mannose receptors for the PME far exceeds that of the mannose binding protein. As new macrophages/monocytes enter the blood stream, the PME is transferred to the new cells from the circulating mannose-binding protein. PME binding to the macrophage/monocyte mannose-binding protein results in the release of an array of cytocommunicators. The cytocommunicators including TNF-α, IL-1β, INF-γ, IL-2, and IL-6 restore to normal the impaired surveillance function of the immune system which had failed in its neoplasm detection function in the cancer patient permitting the patient's immune system of identifying and removing the malignant cells.

*Aloe* polysaccharides in the polymannan extract having molecular weights of 1,000,000, 300,000, 100,000, 50,000 and 25,000 all showed caspase activity. This caspase 3, caspase 9, and cytochrome-C activity is key in the treatment of malignancies by the composition of the present invention, as caspase 3 is a mediator of tumor cell apoptosis. The immune modulatory activity of initiator (apical) caspase 3 and effector (executioner) caspase 3 as well as cytochrome-C have been demonstrated as being extant and are considered to be the mediator system of tumor cell apoptosis.

The inventors tested the composition described herein on 104 patients with different types of cancers. Leukemia and lymphomas were most responsive to the polymannan extract of the present invention (>98%). Prostate, breast, and colon cancers were also responsive to the polymannan extract of the present invention. For the testing the polyamman extract was adminsiteres as an injection. 10 mg of the polymannan extract was reconstituted in sterile water for injection to give a final concentration of ~10 mg/mL. This was injected 2 to 3 times a week. The serum samples from the patients were then taken at regular intervals and monitored for caspase 3 activity.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof"

is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

U.S. Pat. No. 7,196,072: High Molecular Weight Polysaccharide Fraction From *Aloe Vera* with Immunostimulatory Activity.
U.S. Pat. No. 6,083,508: Method of Processing *Aloe* Leaves.
United States Patent Application No. 2006/0084629: Immune System Activating Formula Composed of Selected Long Chain Polysaccharides From Natural Sources.
[1] Pugh N., Ross S. A., ElSohly M. A., and Pasco, D. S. (2001). Characterization of Aloeride, a new high-molecular weight polysaccharide from *Aloe vera* with potent immunomodulatory activity. J. Agr. Food Chem., 49, 1030-1034.

What is claimed is:

1. A method for preparing a fine powder of a polymannan extract comprising the steps of:
   weighing a specified quantity of a freeze-dried *aloe* powder, wherein the quantity is corrected for a moisture content;
   dissolving the freeze-dried *aloe* powder in deionized water to form a solution;
   adding a first volume of an organic solvent to the solution to form a first mixture; wherein the organic solvent to the deionized water ratio is at least 2.5:1;
   allowing the first mixture to settle for at least 8 hours;
   withdrawing a specified volume of a supernatant solution from the first mixture and adding a second volume of the organic solvent to the specified volume of the supernatant solution to form a second mixture;
   centrifuging the second mixture;
   observing for a presence of a precipitate in the second mixture;
   adding a third volume of the organic solvent to the first mixture if any precipitate is observed in second mixture;
   decanting the supernatant of the first mixture by siphoning, wherein the decantation is done only if no precipitate is observed in the second mixture;
   filtering the precipitate from the first mixture by using a filter paper and a suction funnel under vacuum;
   recovering the powder of the polymannan extract from the suction funnel by scraping;
   placing the powder of the polymannan extract in a capped lyophilization flask in a freezer for at least 8 hours;
   lyophilizing the frozen powder of the polymannan extract in a lyophilizer; and
   grinding the lyophilized powder of the polymannan extract in a grinder to a desired texture.

2. The method of claim 1, further comprising the step of weighing, labeling, and storing the fine powder of the polymannan extract in a container.

3. The method of claim 1, wherein the freeze-dried *aloe* powder is derived from an *Aloe* species selected from the group consisting of *Aloe vera, Aloe arborescens, Aloe aristata, Aloe dichotoma, Aloe nyeriensis, Aloe variegate, Aloe barbadensis,* and *Aloe wildii*.

4. The method of claim 1, wherein the organic solvent is selected from the group consisting of methanol, ethanol, isopropyl alcohol, and propanol.

5. The method of claim 1, wherein the freeze-dried *aloe* powder comprises *aloe* polysaccharides, wherein the *aloe* polysaccharides comprise one or more small chain, medium chain, large chain, very-large chain polysaccharides, or any combinations thereof.

6. The method of claim 5, wherein the *aloe* polysaccharides further comprise simple sugars, selected from the group consisting of glucose, mannose, arabinose, and galactose.

7. The method of claim 5, wherein the *aloe* polysaccharides have a molecular weight ranging from 11,500 Daltons to 10,000,000 Daltons.

8. The method of claim 1, wherein the freeze-dried *aloe* powder has at least 25% of *aloe* polysaccharides.

9. The method of claim 1, wherein the freeze-dried *aloe* powder has from 25% *aloe* polysaccharides to 95% *aloe* polysaccharides.

10. The method of claim 1, wherein the freeze dried *aloe* powder comprises at least 14% of *aloe* polysaccharides having a molecular weight of 66,000 Daltons.

11. The method of claim 1, wherein the freeze dried *aloe* powder comprises at least 9% of *aloe* polysaccharides having a molecular weight of 480,000 Daltons.

12. The method of claim 1, wherein the freeze dried *aloe* powder comprises at least 3.5% of *aloe* polysaccharides having a molecular weight of 1,000,000 Daltons.

13. The method of claim 1, wherein the freeze dried *aloe* powder comprises at least 2.4% of *aloe* polysaccharides having a molecular weight of 2,000,000 Daltons.

14. The method of claim 1, wherein the amount of *aloe* polysaccharides having a molecular weight of 2,000,000 Daltons in the freeze dried *aloe* powder ranges from 1.32%-6.36%.

15. The method of claim 1, wherein the amount of *aloe* polysaccharides having a molecular weight of 1,000,000 Daltons in the freeze dried *aloe* powder ranges from 2.55%-3.89%.

16. The method of claim 1, wherein the amount of *aloe* polysaccharides having a molecular weight of 480,000 Daltons in the freeze dried *aloe* powder ranges from 63.85%-73.36%.

17. The method of claim 1, wherein the freeze dried *aloe* powder may contain one or more residual small molecular weight species, selected from the group consisting of glucose, organic acids, lactic acid, malic acid, citric acid, and aspartic acid.

18. The method of claim 17, wherein the one or more residual small molecular weight species are present in amounts ranging from 14%-24% by weight.

* * * * *